(12) United States Patent
Wang et al.

(10) Patent No.: US 9,422,206 B2
(45) Date of Patent: Aug. 23, 2016

(54) PROCESS FOR MAKING LUBE BASE STOCKS FROM RENEWABLE FEEDS

(71) Applicant: ExxonMobil Research and Engineering Company, Annandale, NJ (US)

(72) Inventors: Kun Wang, Bridgewater, NJ (US); Randall D. Partridge, Califon, NJ (US); Himanshu Gupta, Lorton, VA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 166 days.

(21) Appl. No.: 14/096,322

(22) Filed: Dec. 4, 2013

(65) Prior Publication Data

US 2014/0171703 A1 Jun. 19, 2014

Related U.S. Application Data

(60) Provisional application No. 61/738,464, filed on Dec. 18, 2012.

(51) Int. Cl.
*C10G 45/58* (2006.01)
*C10G 45/48* (2006.01)
(Continued)

(52) U.S. Cl.
CPC . *C07C 1/22* (2013.01); *C07C 45/48* (2013.01); *C10G 3/42* (2013.01); *C10G 3/46* (2013.01);
(Continued)

(58) Field of Classification Search
CPC .................................. C07C 1/22; C10G 45/58
USPC .................................................. 585/253, 254
See application file for complete search history.

(56) References Cited

U.S. PATENT DOCUMENTS 7,815,694 B2 10/2010 Miller
7,850,841 B2 12/2010 Koivusalmi et al.
(Continued)

FOREIGN PATENT DOCUMENTS

GB 347543 A 4/1931
WO 2007068800 6/2007

OTHER PUBLICATIONS

Renz, M. "Ketonization of Carboxylic Acids by Decarboxylation: Mechanism and Scope", Eur. J. Org. Chem., (2005), pp. 979-988.*
(Continued)

*Primary Examiner* — In Suk Bullock
*Assistant Examiner* — Aaron Pierpont
(74) *Attorney, Agent, or Firm* — Robert A. Migliorini

(57) ABSTRACT

Provided are processes for making hydrocarbons from renewable feed sources. In an embodiment, there is provided a method for producing a lube basestock including: contacting a compound of Formula (I) and a feedstock of biological origin with a catalyst component including a basic material:

Formula (I)

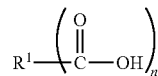

wherein $R^1$ is selected from acyclic hydrocarbyl, cyclic hydrocarbyl, and aryl, wherein $R^1$ has one or more optional substitutions selected from the group consisting of —$R^a$, —$OR^a$, —$C(O)R^a$, and —$C(O)OR^a$, wherein $R^a$ is H or $C_1$-$C_6$ alkyl group; and n is 1, 2, 3, 4 or 5; and hydrogenating a ketone to a hydrocarbon with a catalyst including a hydrogenation catalyst and a hydrothermally stable binder.

34 Claims, 7 Drawing Sheets

(51) Int. Cl.
*C10M 105/02* (2006.01)
*C10M 101/00* (2006.01)
*C07C 1/22* (2006.01)
*C07C 45/48* (2006.01)
*C10G 3/00* (2006.01)
*C07C 1/207* (2006.01)

(52) U.S. Cl.
CPC .. *C10G 3/47* (2013.01); *C10G 3/49* (2013.01); *C10G 3/50* (2013.01); *C10G 45/58* (2013.01); *C10M 101/00* (2013.01); *C10M 105/02* (2013.01); *C07C 1/2072* (2013.01); *C07C 1/2076* (2013.01); *C07C 1/2078* (2013.01); *C10G 2300/1011* (2013.01); *C10N 2230/64* (2013.01); *C10N 2270/00* (2013.01); *Y02P 30/20* (2015.11)

(56) References Cited

U.S. PATENT DOCUMENTS

| | | | |
|---|---|---|---|
| 7,888,542 B2 | 2/2011 | Koivusalmi et al. | |
| 7,960,596 B2 | 6/2011 | Miller | |
| 8,124,572 B2 | 2/2012 | Miller | |
| 8,187,344 B2 | 5/2012 | Jakkula et al. | |
| 2007/0135663 A1* | 6/2007 | Aalto | C10M 105/04 585/1 |
| 2007/0135669 A1 | 6/2007 | Koivusalmi et al. | |
| 2007/0161832 A1 | 7/2007 | Myllyoja et al. | |
| 2008/0302001 A1* | 12/2008 | Koivusalmi | C10G 45/62 44/308 |
| 2009/0014354 A1 | 1/2009 | Knuuttila et al. | |
| 2009/0158637 A1 | 6/2009 | McCall et al. | |
| 2009/0162264 A1 | 6/2009 | McCall et al. | |
| 2009/0193709 A1* | 8/2009 | Marker | C01B 3/16 44/308 |
| 2009/0283442 A1 | 11/2009 | McCall et al. | |
| 2010/0018108 A1 | 1/2010 | Miller | |
| 2010/0056833 A1* | 3/2010 | Suarez | C10G 3/00 585/240 |
| 2010/0081809 A1 | 4/2010 | Devarakonda et al. | |
| 2010/0093568 A1* | 4/2010 | Tagawa | C10M 101/02 508/133 |
| 2010/0234654 A1 | 9/2010 | Wang et al. | |
| 2011/0105813 A1* | 5/2011 | Roberts, IV | C10G 45/58 585/20 |
| 2011/0107656 A1 | 5/2011 | Miller | |
| 2012/0102827 A1 | 5/2012 | Miller | |
| 2012/0102828 A1 | 5/2012 | Miller | |
| 2012/0108869 A1 | 5/2012 | Miller et al. | |
| 2012/0108870 A1 | 5/2012 | Miller | |
| 2012/0108871 A1 | 5/2012 | Miller | |
| 2012/0316093 A1 | 12/2012 | Zhan | |

OTHER PUBLICATIONS

The International Search Report and Written Opinion of PCT/US2013/073016 dated Feb. 24, 2014.

* cited by examiner

PROCESS FOR MAKING LUBE BASE STOCKS FROM RENEWABLE FEEDS

CROSS-REFERENCE TO RELATED APPLICATIONS

This application claims priority to U.S. Provisional Application Ser. No. 61/738,464 filed Dec. 18, 2012, herein incorporated by reference in its entirety.

FIELD

The present disclosure relates to improved methods for making lube basestocks from renewable feed sources.

BACKGROUND

Lube basestocks are commonly used for the production of lubricants, such as lubricating oils for automobiles, industrial lubricants and lubricating greases. They are also used as process oils, white oils, metal working oils and heat transfer fluids. Finished lubricants consist of two general components, lubricating base oil and additives. Lubricating base oil is the major constituent in these finished lubricants and contributes significantly to the properties of the finished lubricant. In general, a few lubricating base oils are used to manufacture a wide variety of finished lubricants by varying the mixtures of individual lubricating base oils and individual additives.

According to the American Petroleum Institute (API) classifications, lube basestocks are categorized in five groups based on their saturated hydrocarbon content, sulfur level, and viscosity index (Table 1). Lube base oils are typically produced in large scale from non-renewable petroleum sources. Group I, II, and III basestocks are all derived from crude oil via extensive processing, such as solvent extraction, solvent or catalytic dewaxing, and hydroisomerization. Group III base oils can also be produced from synthetic hydrocarbon liquids obtained from natural gas, coal or other fossil resources. Group IV basestocks, the poly (alpha olefins) (PAO), are produced by oligomerization of alpha olefins, such as 1-decene. Group V base oils include everything that does not belong to Groups I-IV, such as naphthenics, polyalkylene glycols (PAG) and esters.

TABLE 1

| | API Classification | | | | |
|---|---|---|---|---|---|
| | Group I | Group II | Group III | Group IV | Group V |
| % Saturates | <90 | ≥90 | ≥90 | Poly alpha-olefins (PAO) | All others not belonging to Group I-IV |
| % S | >0.03 | ≤0.03 | ≤0.03 | | |
| Viscosity Index (VI) | 80-120 | 80-120 | ≥120 | | |

Natural oils derived from biological sources are sometimes used as lubricants, but to a small scale, due to their poor low-temperature properties and hydrolysis instability. The triglyceride esters in natural oils are often hydrolyzed to yield fatty acids, which can be subsequently converted into esters as synthetic lubricants.

For environmental, economical, and regulatory reasons, it is of interest to produce fuels, chemicals, and lube oils from renewable sources of biological origin. So far only esters of renewable and biological origin have been used in applications such as refrigeration compressor lubricants, bio-hydraulic oils and metal working oils. In automotive and industrial lubricants, esters from biological sources are used in very small fractions as additives due to technical problems as well as their high prices. For example, ester base oils can hydrolyze readily producing acids, which in turn cause corrosion on lubricating systems.

In contrast, lube basestocks consisting of hydrocarbons from biological sources do not have those technical problems associated with esters from same sources. Most common biological sources for hydrocarbons are natural oils, which can be derived from plant sources such as canola oil, castor oil, sunflower seed oil, rapeseed oil, peanut oil, soy bean oil, and tall oil, or derived from animal fats. The basic structural unit of natural oils and fats is a triglyceride, which is an ester of glycerol with three fatty acid molecules having the structure below:

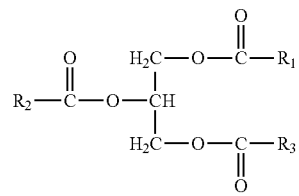

wherein $R_1$, $R_2$, and $R_3$ represent $C_4$-$C_{30}$ hydrocarbon chains. Fatty acids are carboxylic acids containing long linear hydrocarbon chains. Lengths of the hydrocarbon chains most commonly are 18 carbons ($C_{18}$). $C_{18}$ fatty acids are typically bonded to the middle hydroxyl group of glycerol. Typical carbon numbers of the fatty acids linked to the two other hydroxyl groups are even numbers, being between $C_{14}$ and $C_{22}$.

For the purpose of this disclosure, when all the fatty acid chains in a triglyceride have more than 14 carbon atoms, the triglyceride is considered a long-chain fatty acid triglyceride. When one or more of the fatty acid chains in a triglyceride has less than 14 carbon atoms, the triglycerides are considered medium-chain triglycerides.

In the field of fuels, so-called renewable source components are now required both in the US and Europe. Although there is no imminent requirement for lube products currently, generating premium basestocks from renewable sources on a large scale is attractive for the same policy reasons that led to the imposition of regulations in the higher volume fuel area. In fact, with recent advances in biofuels, natural oils are becoming increasingly available as feedstocks that provide fuel value comparable to that of petroleum oils. Converting these bio-feeds to lubes can give significant value uplift.

WO 2007/068800 describes a process for producing a saturated hydrocarbon component from a biological starting material comprising an oligomerization step, an optional pre-hydrogenation step, a deoxygenation step and an optional hydroisomerization step.

US 2009/0014354 mentions a process for producing base oils from a biological starting material comprising a condensation step selected from ketonization, aldol condensation, alcohol condensation and radical reaction and a combined hydrodefunctionalization and isomerization step under pressure from 0.1 to 15 MPa at the temperature from 100 to 500° C. in the presence of a bifunctional catalyst.

Recent researches focus on chemical transformations in a series of catalytic steps requiring separate reactors for each individual step as well as optimization of conditions in each reactor. Many process steps involve clean-up of a reaction mixture or isolation of a desired product from a mixture. For example, fatty acids and alcohols are produced by hydrolysis of fatty acid triglycerides. Hydrolysis is typically conducted by treating the triglyceride with an acid solution, and is sometimes followed by extraction with an organic solvent, and finally recovery of the organic solvent. The acid is consumed in the process and therefore, hydrolysis can add significant cost to the lube processes disclosed in the art.

US 2010/0018108 describes a method for producing base oil and diesel or other transportation fuel comprising processing a triglyceride-containing vegetable oil to effect oligomerization and deoxygenation of unsaturated fatty acid components contained therein to provide for an oligomerized mixture, isomerizing the oligomerized mixture over an isomerization catalyst to yield an isomerized mixture, and distilling the isomerized mixture to produce a base oil and a diesel fuel.

SUMMARY

The present disclosure relates to a process for producing a lube base stock from a feedstock derived from natural oil. There is provided a method for producing a lube basestock comprising: contacting a compound of Formula (I) and a feedstock of biological origin to produce a ketone in the presence of a first catalyst comprising a basic material:

Formula (I)

wherein $R^1$ is selected from the group consisting of acyclic hydrocarbyl, cyclic hydrocarbyl, and aryl, wherein $R^1$ has one or more optional substitutions selected from the group consisting of —$R^a$, —$OR^a$, —$C(O)R^a$, and —$C(O)OR^a$, wherein $R^a$ is H or $C_1$-$C_6$ alkyl group, and n is 1, 2, 3, 4 or 5; and hydrogenating the ketone to a hydrocarbon in the presence of a second catalyst comprising a hydrogenation catalyst and a hydrothermally stable binder. The feedstock normally contains glycerides including triglycerides and/or lipids such as phospholipids or saccharolipids, and can further contain fatty acids, fatty acid esters, fatty alcohols, fatty olefins, monoglycerides, and di-glycerides. The process involves conversion of a starting material containing carboxylic group(s) or ester bond(s) to a hydrocarbon mixture containing hydrocarbons in the $C_{20}$ and higher range suitable for use as lube basestocks and/or diesel fuel. In an embodiment, the hydrogenation catalyst also promotes dewaxing of the relatively unbranched hydrocarbon produced by the action of the basic catalyst on the glyceride- or fatty acid-containing feedstock.

In another embodiment, there is provided a method for producing a lube basestock comprising: coupling a compound of Formula (I) and a compound of Formula (II) in the presence of a first catalyst comprising a basic material to produce a ketone of Formula (III):

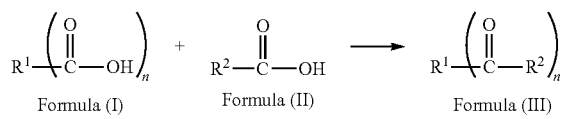

Formula (I)    Formula (II)    Formula (III)

wherein each of $R^1$ and $R^2$ is independently selected from the group consisting of acyclic hydrocarbyl, cyclic hydrocarbyl, and aryl, wherein each of $R^1$ and $R^2$ independently has one or more optional substitutions selected from the group consisting of —$R^a$, —$OR^a$, —$C(O)R^a$, and —$C(O)OR^a$, wherein $R^a$ is H or $C_1$-$C_6$ alkyl group, and n is 1, 2, 3, 4 or 5; and hydrogenating the ketone of Formula (III) to a hydrocarbon in the presence of a second catalyst comprising a hydrogenation catalyst and a hydrothermally stable binder.

In yet another embodiment, there is provided a method for producing a lube basestock comprising: contacting a compound of Formula (I) and a feedstock of biological origin in a single reactor in the presence of a first catalyst comprising a basic material and a second catalyst comprising a hydrogenation catalyst and a hydrothermally stable binder:

Formula (I)

wherein $R^1$ is selected from the group consisting of acyclic hydrocarbyl, cyclic hydrocarbyl, and aryl, wherein $R^1$ has one or more optional substitutions selected from the group consisting of —$R^a$, —$OR^a$, —$C(O)R^a$, and —$C(O)OR^a$, wherein $R^a$ is H or $C_1$-$C_6$ alkyl group, and n is 1, 2, 3, 4 or 5.

DETAILED DESCRIPTION

Figure 1:
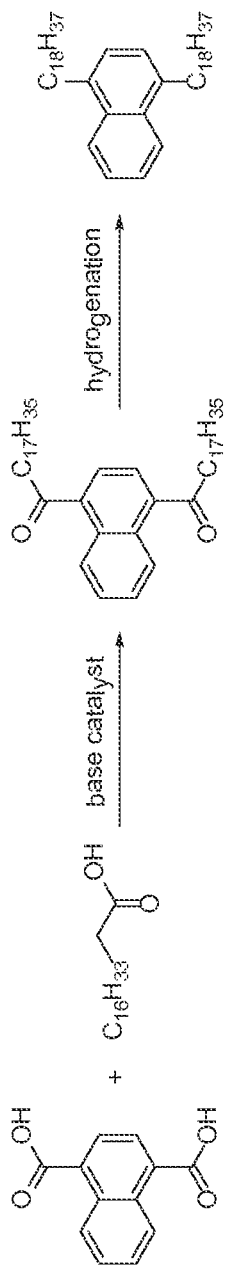
FIG. 1 is a scheme illustrating reactions of a process using stearic acid and 1,4-naphthalene dicarboxylic acid along with a base catalyst and a hydrogenation catalyst.

All numerical values within the detailed description and the claims herein are modified by "about" or "approximately" the indicated value, and take into account experimental error and variations that would be expected by a person having ordinary skill in the art.

"Hydrocarbon" refers to a molecule consisting only of carbon and hydrogen atoms, and "hydrocarbyl" refers to a group/radical consisting only of carbon and hydrogen atoms. In various embodiments, the hydrocarbon has from 1 to 300 carbon atoms.

"Acyclic hydrocarbyl" refers to a straight or branched hydrocarbyl group. In an embodiment, acyclic hydrocarbyl has from 1 to 30 carbon atoms. In various embodiments, acyclic hydrocarbyl is a $C_1$-$C_{22}$ alkyl group.

"Cyclic hydrocarbyl" is a hydrocarbyl group containing at least one saturated or partially unsaturated ring structure. Cyclic hydrocarbyl includes a monocyclic group, a fused bicyclic ring as shown in Formula A1 and two monocyclic groups linked by $C_1$-$C_{12}$ hydrocarbyl chain, for example, as shown in Formula A2 (where X is $C_1$-$C_{12}$ hydrocarbyl linker):

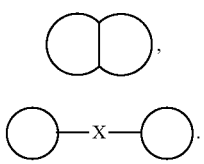

Formula A1

Formula A2

In some embodiments, cyclic hydrocarbyl contains one or two 5- or 6-member rings.

"Aryl" refers to a monocyclic, bicyclic, tricyclic or tetracyclic carbon ring, wherein at least one ring is aromatic. Aryl includes two aromatic rings linked by $C_1$-$C_{12}$ hydrocarbyl chain, for example, as shown in Formula B (where X is $C_1$-$C_{12}$ hydrocarbyl linker).

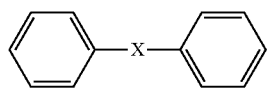

Formula B

Aryl also includes a carbocyclic aromatic ring fused with a 5- or 6-membered cycloalkyl group. Examples of aryl groups include, but are not limited to, phenyl, naphthyl, anthracenyl, phenanthrenyl, tetrahydronaphthyl and indanyl.

In various embodiments, acyclic hydrocarbyl, cyclic hydrocarbyl to and/or aryl groups in this disclosure have one or more optional substitutions selected from the group consisting of —$R^a$, —$OR^a$, —$C(O)R^a$, and —$C(O)OR^a$, wherein $R^a$ is H or $C_1$-$C_6$ alkyl group.

The present disclosure provides a method for producing a lube basestock comprising: contacting a compound of Formula (I) and a feedstock of biological origin to produce a ketone in the presence of a catalyst component comprising a basic material:

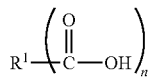

Formula (I)

wherein $R^1$ is as defined above; and hydrogenating the ketone to a hydrocarbon with a catalyst comprising a hydrogenation catalyst and a hydrothermally stable binder. In various embodiments, the hydrogenation catalysts also provide functionality for such conversions as hydrogenation of olefins, acids, and ketones, as well as isomerization to introduce branching to the hydrocarbon molecules and/or provide a dewaxing function.

The compound of Formula (I) is a cyclic or acyclic hydrocarbon molecule having at least one carboxylic functional group (up to five carboxylic groups). In particular embodiments, the compound of Formula (I) has one, two or three carboxylic groups (i.e., n=1, 2 or 3). In some embodiments, the compound of Formula (I) is an acyclic hydrocarbyl containing compound which is selected from sebacic acid, citric acid, and a fatty acid having 14 to 22 carbon atoms such as, for example, myristic acid, palmitic acid and stearic acid. In some other embodiments, the compound of Formula (I) is a cyclic hydrocarbyl containing compound which is selected from cyclohexane 1,2-dicarboxylic acid, cyclohexane 1,3-dicarboxylic acid, and cyclohexane 1,4-dicarboxylic acid. In yet some other embodiments, $R^1$ is aryl which is phenyl or naphthalenyl and n is 1, 2, or 3. Non-limiting examples of aryl containing compounds include naphthalene 1,2-dicarboxylic acid, naphthalene 1,3-dicarboxylic acid, and naphthalene 1,4-dicarboxylic acid.

The feedstock of biological origin normally comprises one or more components selected from the group consisting of fatty acids, fatty acid esters, fatty alcohols, fatty olefins, mono-glycerides, di-glycerides, tri-glycerides, phospholipids and saccharolipids. In various embodiments, the feedstock of biological origin is selected from plant oils such as rapeseed oil, soy bean oil, palm oil, camelina oil, jatropha oil, and jojoba oil; animal fats such as fish oil, lard and beef tallow; and algae oils. In a particular embodiment, the feedstock of biological origin is selected from fatty acids containing 14-22 carbon atoms, rapeseed oil, soy oil, and palm oil.

In certain aspects, the methods described herein are used to produce alkylated aromatic compounds. Such alkylated aromatic compounds include alkylated benzenes and alkylated naphthalenes having the following general formula, respectively:

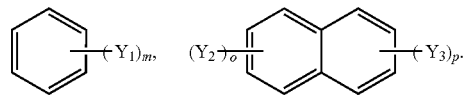

wherein m is 1 to 6 inclusive; o and p are independently 1 to 4 inclusive; and each of $Y_1$, $Y_2$ and $Y_3$ is independently is selected from $C_1$-$C_{30}$ linear alkyl group and $C_3$-$C_{300}$ branched alkyl group. In some embodiments, each of $Y_1$, $Y_2$ and $Y_3$ is independently is selected from $C_1$-$C_{20}$ linear alkyl group and $C_3$-$C_{30}$ branched alkyl group.

In particular aspects, the methods are used to produce alkylated naphthalenes (AN) which are an important class of synthetic fluids. Alkylated naphthalenes have various desirable properties such as, for example, excellent thermo-oxidative stability; excellent hydrolytic stability; better solubility than PAO and Group II and III basestocks; and good additive response such as less surface competition, low volatility, good pour point, excellent lubricity/film thickness, and good seal swelling properties. They can be produced by Friedel-Crafts alkylation of naphthalene using alkyl halides, alcohols, or olefins with a catalyst such as zeolites or solid superacids. Olefins may be preferred alkylating agents since alkyl halides and alcohols generate undesirable by-products such as hydrogen halide and water. Olefins (alpha-, internal-, or branched-) with 8 to 18 carbons are needed in order to generate product with desired molecular weight. With increasingly tight supply of long-chain olefins, it is desirable to find alternative routes to prepare alkylated naphthalenes, where the feed is not constrained by the supply of long-chain olefins.

Figure 2:
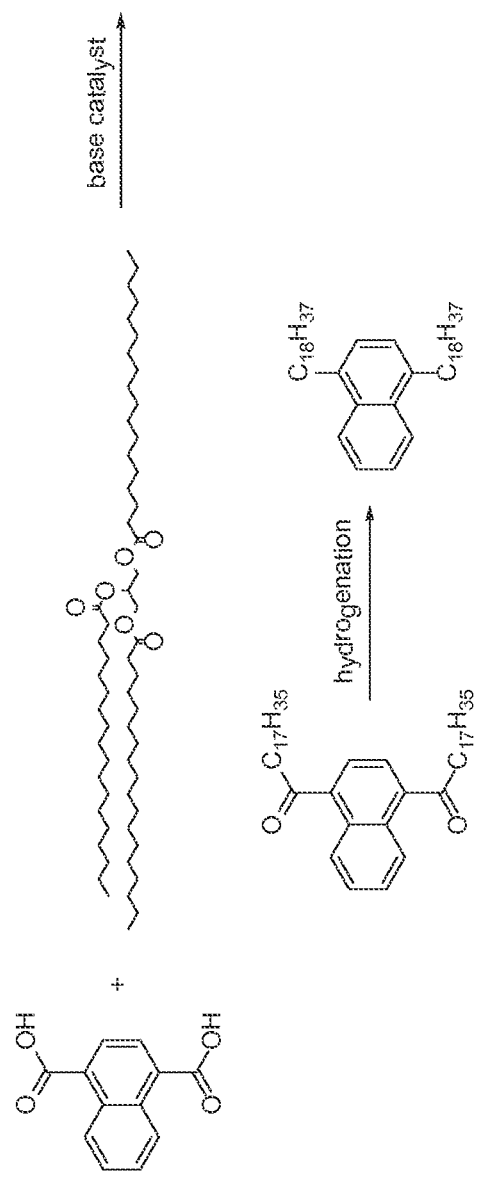
FIG. 2 is a scheme illustrating reactions of a process using triglyceride and 1,4-naphthalene dicarboxylic acid along with a base catalyst and a hydrogenation catalyst.

FIGS. 1 and 2 illustrate specific embodiments of the methods for producing alkylated naphthalenes (AN). In some embodiments, as illustrated in FIGS. 1 and 2, the starting material to be coupled with a naphthalene carboxylic acid is selected from a fatty acid (FIG. 1) and a triglyceride (FIG. 2). In some further aspects, alkyl groups of the products can be isomerized (i.e., addition of methyl branching) to improve low temperature properties using standard hydro-isomerization catalysts.

Figure 3:
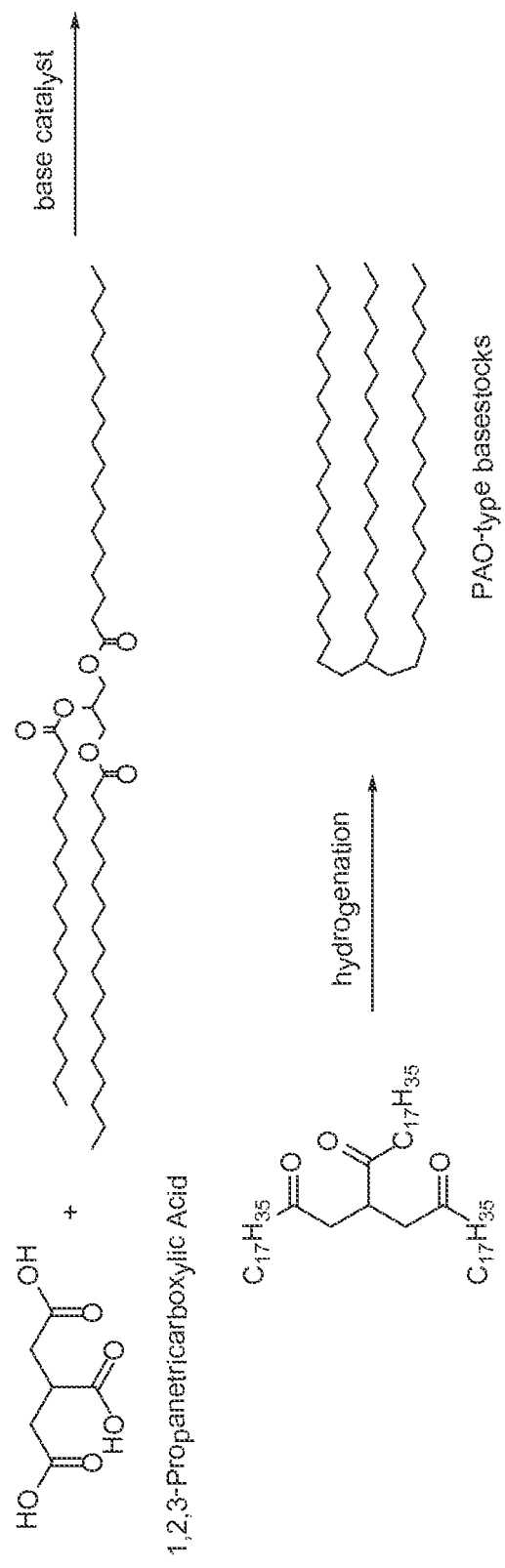
FIG. 3 is a scheme illustrating reactions of a process using triglyceride and 1,2,3-propanecarboxylic acid along with a base catalyst and a hydrogenation catalyst.
Figure 7:
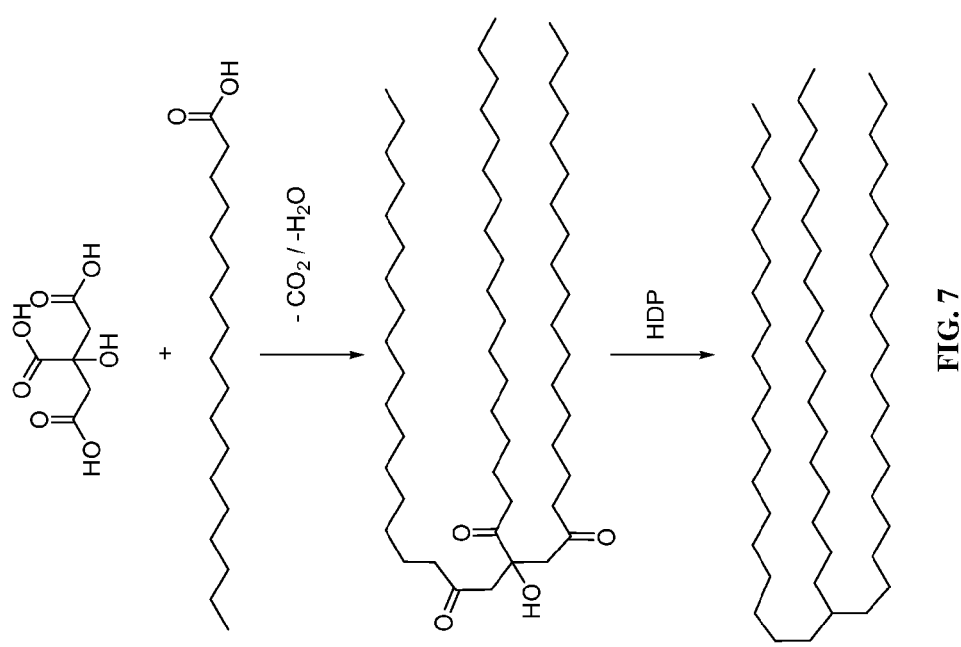
FIG. 7 is a scheme illustrating reactions of a process using citric acid and stearic acid along with a base catalyst and a hydrogenation catalyst (Example 2).

In particular embodiments, the methods are used for the synthesis of PAO type basestocks by reacting fatty acids or triglycerides, for example, as illustrated in FIG. 3 and FIG. 7. In a particular aspect, the method comprises a reaction with 1,2,3-propanetricarboxylic acid and stearic acid or tristearin to produce a tri-ketone which can be converted to an iso-paraffin via hydrogenation (FIG. 3). In another aspect, the method comprises a reaction with citric acid and stearic acid or tristearin to produce a tri-ketone which can be converted to an iso-paraffin via hydrogenation (FIG. 7).

In another embodiment, there is provided a method for producing a lube basestock comprising: coupling a compound of Formula (I) and a compound of Formula (II) in the presence of a catalyst component comprising a basic material to produce a ketone of Formula (III):

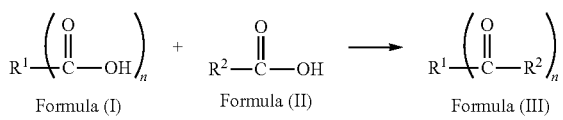

wherein $R^1$ and $R^2$ are as defined above; and hydrogenating the ketone of Formula (III) to a hydrocarbon with a catalyst comprising a hydrogenation catalyst and a hydrothermally stable binder, wherein $R^1$ and $R^2$ can be the same or different. In some particular embodiments, $R^2$ is a fatty acid having 8 to 36 carbons, particularly from 10 to 26 carbons, more particularly from 14 to 22 carbons. In some embodiments, the compound of Formula (II) is selected from saturated or unsaturated $C_{10}$-$C_{22}$ fatty acids such as capric acid ($C_{10}$), lauric acid ($C_{12}$), myristic acid ($C_{14}$), palmitic acid ($C_{16}$), stearic acid ($C_{18}$), oleic acid ($C_{18}$ mono-unsaturated), linoleic acid ($C_{18}$ di-unsaturated), arachidic acid ($C_{20}$), and behenic acid ($C_{22}$).

In yet another embodiment, there is provided a method for producing a lube basestock comprising: contacting a compound of Formula (I) and a feedstock of biological origin in the presence of catalyst components comprising a basic material and a catalyst comprising a hydrogenation catalyst and a hydrothermally stable binder in a single reactor:

Formula (I)

wherein $R^1$ as defined above.

Further description of the feedstock, catalytic components, reaction conditions, and product properties for the various embodiments of the disclosure to is given below. Except where the context provides otherwise, it is to be understood that the description of starting materials, catalysts, conditions, and products is generally applicable to all aspects and embodiments of the disclosure described and/or claimed herein.

Feedstocks

Feedstocks for the process are drawn either from petroleum sources or from renewable sources of biological origin, e.g., plant, algae or animal (including insect) origin. Animal, algae and plant oils containing tri-glycerides, as well as partially processed oils containing mono-glycerides and di-glycerides are included in this group. Another source of feedstock is phospholipids or saccharolipids containing fatty acid esters in their structure, such as phosphatidyl choline and the like present in plant cell walls. Carbon numbers for the fatty acid component of such feedstocks are generally in the range of $C_2$ or greater, up to $C_{30}$.

Other components of the feed can include a) plant fats, plant oils, plant waxes; animal fats, animal oils, animal waxes: fish fats, fish oils, fish waxes, and mixtures thereof; b) free fatty acids or fatty acids obtained by hydrolysis, acid trans-esterification or pyrolysis reactions from plant fats, plant oils, plant waxes, animal fats, animal oils, animal waxes, fish fats, fish oils, fish waxes, and mixtures thereof; c) esters obtained by trans-esterification from plant fats, plant oils, plant waxes, animal fats, animal oils, animal waxes, fish fats, fish oils, fish waxes, and mixtures thereof; d) esters obtained by esterification of free fatty acids of plant, animal and fish origin with alcohols, and mixtures thereof; e) fatty alcohols obtained as reduction products of fatty acids from plant fats, plant oils, plant waxes, animal fats, animal oils, animal waxes, fish fats, fish oils, fish waxes, and mixtures thereof; and f) waste and recycled food grade fats and oils, and fats, oils and waxes obtained by genetic engineering, and mixtures thereof.

Examples of vegetable oils that can be used in accordance with this disclosure include, but are not limited to rapeseed (canola) oil, soybean oil, coconut oil, sunflower oil, palm oil, palm kernel oil, peanut oil, linseed oil, tall oil, corn oil, castor oil, jatropha oil, jojoba oil, olive oil, flaxseed oil, camelina oil, safflower oil, babassu oil, tallow oil and rice bran oil. Vegetable oils as referred to herein can also include processed vegetable oil material as a portion of the feedstock. Non-limiting examples of processed vegetable oil material include fatty acids and fatty acid alkyl esters. Alkyl esters typically include $C_1$-$C_5$ alkyl esters. One or more of methyl, ethyl, and propyl esters are desirable.

Examples of animal fats that can be used in accordance with the disclosure include, but are not limited to, beef fat (tallow), hog fat (lard), turkey fat, fish fat/oil, and chicken fat. The animal fats can be obtained from any suitable source including restaurants and meat production facilities.

Animal fats as referred to herein also include processed animal fat material. Non-limiting examples of processed animal fat material include fatty acids and fatty acid alkyl esters. Alkyl esters typically include $C_1$-$C_5$ alkyl esters. In particular embodiments, alkyl esters are one or more of methyl, ethyl, and propyl esters.

Algae oils or lipids can typically be contained in algae in the form of membrane components, storage products, and/or metabolites. Certain algal strains, particularly microalgae such as diatoms and cyanobacteria, can contain proportionally high levels of lipids. Algal sources for the algae oils can contain varying amounts, e.g., from 2 wt % to 40 wt % of lipids, based on total weight of the biomass itself.

Algal sources for algae oils can include, but are not limited to, unicellular and multicellular algae. Examples of such algae can include a rhodophyte, chlorophyte, heterokontophyte, tribophyte, glaucophyte, chlorarachniophyte, euglenoid, haptophyte, cryptomonad, dinoflagellum, phytoplankton, and the like, and combinations thereof. In one embodiment, algae can be of the classes Chlorophyceae and/or Haptophyta. Specific species can include, but are not limited to, *Neochloris oleoabundans, Scenedesmus dimorphus, Euglena gracilis, Phaeodactylum tricornutum, Pleurochrysis carterae, Prymnesium parvum, Tetraselmis chui*, and *Chlamydomonas reinhardtii*. Additional or alternate algal sources can include one or more microalgae of the *Achnanthes, Amphiprora, Amphora, Ankistrodesmus, Asteromonas,*

*Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Platymonas, Pleurochrysis, Pleurococcus, Prototheca, Pseudochlorella, Pyramimonas, Pyrobotrys, Scenedesmus, Skeletonema, Spyrogyra, Stichococcus, Tetraselmis, Thalassiosira, Viridiella,* and *Volvox* species, and/or one or more cyanobacteria of the *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, lyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tvchonema,* and *Xenococcus* species.

Other feeds usable in the present disclosure can include any of those that comprise primarily triglycerides and free fatty acids (FFAs). The triglycerides and FFAs typically contain aliphatic hydrocarbon chains in their structure having from 8 to 36 carbons, particularly from 10 to 26 carbons, for example from 14 to 22 carbons. Types of triglycerides can be determined according to their fatty acid constituents. The fatty acid constituents can be readily determined using Gas Chromatography (GC) analysis. This analysis involves extracting the fat or oil, saponifying (hydrolyzing) the fat or oil, preparing an alkyl (e.g., methyl) ester of the saponified fat or oil, and determining the type of (methyl) ester using GC analysis. In one embodiment, a majority (i.e., greater than 50%) of the triglyceride present in the lipid material is made of $C_{10}$ to $C_{26}$ fatty acid constituents, based on total triglyceride present in the lipid material. Further, a triglyceride is a molecule having a structure identical to the reaction product of glycerol and three fatty acids. Thus, although a triglyceride is described herein as being comprised of fatty acids, it should be understood that the fatty acid component does not necessarily contain a carboxylic acid hydrogen. If triglycerides are present, a majority of triglycerides present in the feed can particularly be comprised of $C_{12}$ to $C_{22}$ fatty acid constituents, based on total triglyceride content. Other types of feed that are derived from biological raw material components can include fatty acid esters, such as fatty acid alkyl esters (e.g., FAME and/or FAEE).

For reactions with feedstocks having a relatively higher degree of unsaturation, an acidic catalyst can be used to promote dimerization and oligomerization. The dimers and oligomers are branched or having cyclic structures, which can be coupled with another carboxylic acid forming ketones of higher carbon numbers. Subsequent hydrogenation under the action of the hydrogenation catalyst produces saturated, branched or cyclized hydrocarbons than can be naturally very low in wax and require little if any dewaxing. If the feedstock is highly saturated, action of a basic catalyst produces straight chain products that are subsequently hydrogenated to relatively straight chain hydrocarbons that normally require some dewaxing to make them suitable lube stocks. Dewaxing can be provided by the hydrogenation catalyst, as further described below.

One method for characterizing the triglycerides in a feedstock is based on the number of carbons in the side chains. While some feedstocks may have consistent numbers of carbons in each side chain, such as in a tristearin feedstock, many types of triglycerides will have variations in chain length between molecules and even within molecules. In order to characterize these variations, the average number of carbons per side chain in the triglycerides can be determined. By definition, a triglyceride contains three side chains. Each side chain contains a number of carbons, as mentioned above. By averaging the number of carbons in each side chain for the triglycerides in a feedstock, an average side chain length can be determined. The average number of carbons (also referred to as average carbon number) per side chain in the feedstock can be used as a comparative value for characterizing products. For example, the average number of carbons per side chain in the feedstock can be compared with the average number of carbons in hydrocarbons generated by converting and/or isomerizing the triglyceride-containing feedstock.

In various aspects, the production of carboxylic acid coupling products and corresponding hydrogenated products is based on processing of triglycerides within the feed. Thus, in some embodiment, the presence of at least some triglycerides within the feed is desirable. The feed can include at least 10 wt % of feed based on a renewable source or sources, such as at least 25 wt %. In particular embodiments, the renewable portion of the feed is at least 50 wt %, or at least 75 wt %, or at least 90 wt %, or at least 95 wt %. Such higher amounts of feed from a renewable source provide an advantage based on the greater amount of renewable material. Additionally or alternately, the feed can be entirely a feed from a renewable source, or the feed can include 99 wt % or less of a feed based on a renewable source, or 90 wt % or less, or 75 wt % or less, or 50 wt % or less.

Higher amounts of feed from a renewable source provide an advantage based on the greater amount of renewable material, as well as potentially including a greater amount of triglycerides. Feeds with lower amounts of renewable materials may have other processing advantages. Such advantages can include improved flow characteristics within a reaction system, as renewable feeds often have a relatively high viscosity compared to conventional diesel or lubricant feeds in a refinery. Additionally, deoxygenation of a renewable feed can generate a substantial amount of heat due to formation of highly favorable products from a free energy standpoint, such as $H_2O$ and $CO_2$. For a typical catalyst bed with a bed length of 25 to 30 feet (9 to 10 meters), it may be preferable to have a temperature increase across the bed of 100° F. (55° C.) or less. If deoxygenation of a renewable feed with high oxygen content is performed using a sufficiently reactive catalyst, an exotherm of greater than 100° F. across the catalyst bed can be generated. Blending a renewable feed with a portion that does not contain oxygen can reduce the exotherm generated across a catalyst bed used for performing deoxygenation.

Thus the feedstock can contain a number of components. It can be supplied as a solution in a suitable solvent (particularly a non-reactive solvent such as a hydrocarbon), or the feedstock can be supplied neat. The main reactions are thought to be coupling or oligomerizing the fatty acid components (which produces intermediate products of suitable carbon number to be useful as lube base stocks upon hydrogenation), and hydrogenating the resulting products to remove functional groups and produce a saturated hydrocarbon.

The feed may contain various amount of mineral feed as diluent. The advantages of increased mineral feed content are largely due to dilution of the renewable feed, as the processing conditions effective for deoxygenation of a renewable feed will have a low or minimal impact on a typical hydroprocessed mineral feed. Therefore, while the deoxygenation conditions are effective for deoxygenation of renewable feeds at a variety of blend ratios with mineral feeds, it may be preferable to have at least 75 wt % of the feed from a renewable source, such as at least 90 wt % or at least 95 wt %.

One option for increasing the renewable content of a feed while retaining some of the benefits of adding a feed with reduced oxygen content is to use recycled product from processing of renewable feed as a diluent. A recycled product from processing a renewable feed is still derived from a renewable source, and therefore such a recycled product is counted as a feed portion from a renewable source. Thus, a feed containing 60% renewable feed that has not been processed and 40% of a recycled product from processing of the renewable feed would be considered as a feed that includes 100% of feed from a renewable source. As an example, at least a portion of the product from processing of a renewable feed can be a diesel boiling range product. Such a recycled diesel boiling range product will be deoxygenated, and therefore incorporation of the recycled diesel boiling range product in the feed will reduce the exotherm generated during deoxygenation. Adding a recycled diesel boiling range product is also likely to improve the cold flow properties of a renewable feed. More generally, any convenient product from processing of a renewable feed can be recycled for blending with the renewable feed in order to improve the cold flow properties and/or reduce the oxygen content of the input flow to a deoxygenation process. If a recycled product flow is added to the input to a deoxygenation process, the amount of recycled product can correspond to at least 10 wt % of the feed to the deoxygenation process, such as at least 25 wt %, or at least 40 wt %. Additionally or alternately, the amount of recycled product in a feed can be 60 wt % or less, such as 50 wt % or less, 40 wt % or less, or 25 wt % or less.

With regard to triglyceride content, the feedstock can include at least 10 wt %, such as at least 25 wt %, and particularly at least 40 wt %, or at least 60 wt %, or at least 80 wt %. Additionally or alternately, the feed can be composed entirely of triglycerides, or the triglyceride content of the feed can be 90 wt % or less, such as 75 wt % or less, or 50 wt % or less. The methods described herein are suitable for conversion of triglycerides to lubricant products, so higher contents of triglycerides may be advantageous. However, to the degree that a recycle loop is used to improve the feed flow properties or reduce the reaction exotherm across catalyst beds, lower triglyceride contents may be beneficial.

While feed dilution can be used to control the exotherm generated across a catalyst bed used for deoxygenation, it is noted that some processing options can also impact the exotherm. One alternative is to use a less reactive catalyst, so that a larger amount of catalyst is needed at a given liquid hourly space velocity (LHSV) in order to deoxygenate a feed to a desired level. Another option is to reduce the amount of hydrogen provided for the deoxygenation process. Still another option could be to introduce additional features into a reactor to assist in cooling and/or transporting heat away from a deoxygenation catalyst bed. In combination with selecting an appropriate amount of product recycle and/or blending of another non-oxygenated feed, a desired combination of a flow characteristics and heat generation during deoxygenation can be achieved.

Oxygen is the major heteroatom component in renewable base feeds. A renewable feedstream based on a vegetable oil, prior to hydrotreatment, includes up to 10 wt % oxygen, for example up to 12 wt % or up to 14 wt %. Such a renewable feedstream, also called a biocomponent feedstream, normally includes at least 1 wt % oxygen, for example at least 2 wt %, at least 3 wt %, at least 4 wt %, at least 5 wt %, at least 6 wt %, or at least 8 wt %. Further, the renewable feedstream, prior to hydrotreatment, can include an olefin content of at least 3 wt %, for example at least 5 wt % or at least 10 wt %.

Biocomponent based feedstreams have a wide range of nitrogen and/or sulfur contents depending on the feed sources. For example, a feedstream based on a vegetable oil source can contain up to 300 wppm nitrogen. In some embodiments, the sulfur content can be 500 wppm or less, for example 100 wppm or less, 50 wppm or less, or 10 wppm or less, where wppm stands for parts per million by weight.

Catalysts—Definition

Catalysts that have sufficient acidic or basic properties to be effective in coupling carboxylic acids such as fatty acids, fatty acid esters, fatty alcohols, fatty olefins, or glycerides (mono-, di-, or tri-glycerides) can be identified by determining the molar ratio of chemisorption of $CO_2$ and $NH_3$ over these materials. $CO_2$, a weak acid, is used to titrate the basic sites present on the catalysts. Likewise, $NH_3$, a strong base, is titrated to indicate the acidic sites on these materials. Many factors determine the actual amount of chemisorption, such as surface area of the material (often significantly affected by the catalyst preparation method), the temperature at which the chemisorption is measured, and the pressure at which the chemisorption is tested. The ratio of adsorbed $CO_2$ and $NH_3$ indicates a relative acidity or basicity.

For the present purposes, a "basic" catalyst is defined as material having a molar ratio of chemisorption of $CO_2$ per gram of material to the chemisorption of $NH_3$ per gram of material greater than 0.5, typically greater than 0.75, and especially greater than 1.0, when tested as described below. In non-limiting examples, the "carbon dioxide/ammonia ratio" ranges from 1.0 to 100; particularly from 1.0 to 50; or more particularly from 1.0 to 40.

An "acidic" catalyst is defined as catalyst having a carbon dioxide/ammonia ratio of less than 0.5. typically less than 0.3, and especially less than 0.2, when tested as described below. In various embodiments, the values range from 0.05 to 0.5; particularly from 0.05 to 0.3; or more particularly from 0.05 to 0.2.

Determination of carbon dioxide/ammonia ratio (i.e. the molar ratio of chemisorption of $CO_2$ per gram of catalyst to the chemisorption of $NH_3$ per gram of catalyst) is conducted using a Mettler TGA/SDTA 851 thermogravimetric analysis system at ambient pressure. The catalyst sample is calcined in flowing air at 500° C. for three hours or at least until a constant sample weight is obtained. The temperature of the sample is then reduced in flowing air (helium could also be used) to the desired temperature of chemisorption. Next, the sample is allowed to equilibrate at the desired temperature in flowing helium and weighed. Chemisorption of carbon dioxide is measured at 150° C., and chemisorption of ammonia is measured at 250° C. After being weighed, the sample is subjected to a number of pulses (12 seconds/pulse) of gaseous mixture containing helium and either carbon dioxide or ammonia until a constant weight is obtained. The gas mixture contains 10 mole percent carbon dioxide or ammonia with the remainder being helium. After each pulse of the gas mixture being tested, the sample is flushed with flowing helium for 3 minutes. 20 separate pulses of the gas mixture are used in each test. The increase in weight of the sample in terms of mg/g material based on the sample weight after calcination is used to determine the moles of $CO_2$ or $NH_3$ adsorbed per gram of material.

Molar ratios of chemisorption of $CO_2$ to the chemisorption of $NH_3$ per gram of material for some representative catalysts are shown in Table 2.

TABLE 2

| Materials | $CO_2/NH_3$ Chemisorption Molar Ratio |
|---|---|
| MgO (Elastomag 170) | 7.82 |
| MgO (MagChem 200AD) | 6.92 |
| γ-$Al_2O_3$ (Alfa # 43832) | 0.47 |
| Hydrotalcite (Pural MG30) | 1.35 |
| Hydrotalcite (Pural MG63) | 1.95 |
| Hydrotalcite (Pural MG70) | 2.30 |
| W/$ZrO_2$ | 0.07 |
| $La_2O_3$ | 6.64 |
| La/$SiO_2$ | 0.92 |
| $AlPO_x$ | 0.75 |
| $NdAlPO_x$ | 1.04 |
| $YAlPO_x$ | 0.86 |
| $PrAlPO_x$ | 1.05 |
| La/$ZrO_2$ (700° C. calcined) | 1.06 |
| $Y_2O_3$—5% $ZrO_2$ | 6.17 |
| $Y_2O_3$—25% $ZrO_2$ | 1.18 |
| $Nd_2O_3$ | 35.37 |
| $Sm_2O_3$ | 15.61 |
| $Y_2O_3$ | 14.95 |
| $CeO_2$ | 8.48 |
| $Pr_2O_3$ | 1.56 |
| $TiO_2$ | 0.55 |
| $ZrO_2$ | 0.33 |
| SAPO-34 | 0.19 |
| ZSM-5 | 0.16 |
| $SiO_2$ | 0.02 |
| USY | 0.00 |
| 75/25 $SiO_2/Al_2O_3$ | 0.38 |
| 50/50 $SiO_2/Al_2O_3$ | 0.47 |
| 25/25 $SiO_2/Al_2O_3$ | 0.41 |
| 13/87 $SiO_2/Al_2O_3$ | 0.42 |
| $La_2O_3/SiO_2$ | 0.92 |
| MCM-41 | 0.44 |

Catalysts suitable for use to couple carboxylic acids such as fatty acids, fatty acid esters, fatty alcohols, fatty olefins, or glycerides (mono-, di-, or tri-glycerides) are drawn from oxides and mixed oxides of metals of Group 1 to Group 6, Group 12 to Group 15, Lanthanide Series, or Actinide Series of the Periodic Table of Elements. The catalysts can also comprise acidic or basic clays such as hydrotalcites, bentonite, montmorillonite, aluminosilicates such as zeolites, aluminophosphates, or metalloaluminophosphates (where metal is, for example, Si, Nd, Y, Pr, Ce, Ti, or Zr).

In one embodiment, the coupling catalysts comprise two or more metal oxides, particularly one Group 4 metal oxide and one or more selected from Group 2, Group 3, Lanthanide Series, and Actinide Series metal oxides. Yet in another embodiment, the coupling catalysts are selected from oxides of Group 2, Group 12, or Group 13 elements, and mixtures thereof. In another embodiment, the coupling catalysts are either naturally occurring or synthetic clays such as hydrotalcite, bentonite, montmorillonite, or mixtures thereof. Compositions for each individual component in the oxide mixtures can vary within the range of 1-99%. The oxides can be prepared using a variety of methods, although generally they are prepared by converting a suitable precursor by precipitation from solution and/or calcination. Suitable precursors include metal salts, such as halides, sulfates, phosphates, halides, nitrates, hydroxides, oxychlorides, alkoxides, and acetates.

In one embodiment, a metal oxide useful as a catalyst is produced by first preparing a liquid solution comprising a salt of the metal in a solvent, such as water. The resultant solution is then subjected to conditions sufficient to cause precipitation of the solid oxide material, such as by the addition of a precipitating reagent, typically a base such as sodium hydroxide or ammonium hydroxide. The liquid solution is generally maintained at a temperature at or below 200° C. during the precipitation, for example in the range of from 0° C. to 200° C., such as from 20° C. to 100° C. In an embodiment, the resulting gel is hydrothermally treated at a temperature of at least 80° C., particularly at least 100° C., for up to 10 days, such as up to 5 days, for example up to 3 days. The resulting material is then recovered, for example by filtration or centrifugation, washed, and dried. The resulting particulate material is typically then calcined, normally in an oxidizing atmosphere, at a temperature of at least 400° C., such as from 400° C. to 800° C. for up to 48 hours, such as for 0.5 hours to 24 hours, for example for 1 hour to 10 hours.

When two or more metal oxides are used for the coupling of fatty acids, fatty acid esters, fatty alcohols, fatty olefins, or glycerides (mono-, di-, or tri-glycerides), they may either be co-precipitated or precipitated separately and combined with each other at any later stage of processing including as calcined solid particles.

Basic Catalysts

Coupling of carboxylic acids such as fatty acids forming ketones (ketonic decarboxylation), for example, is catalyzed by a component having adequate basicity to catalyze the reaction. They are referred to herein as base catalysts, basic catalysts, basic materials, or other similar phrases. It is believed that basic catalysts promote the hydrolysis of triglyceride into fatty acids and the coupling of the fatty acids. Advantageously, catalysis by a basic catalyst or catalyst component leads to coupling of acid components to form chemical species having carbon number in the $C_{24}$ and higher range. This conveniently produces hydrocarbons (after subsequent hydrogenation in the presence of other catalysts) that are suitable as lube base stocks.

According to the definitions used here, basic catalysts are a class of materials with the "carbon dioxide/ammonia ratio" in the range of 1-100; particularly from 1.0 to 50; or more particularly from 1.0 to 40. Examples of suitable basic catalyst components include, but are not limited to, basic clays such as a hydrotalcite; an alkali impregnated support such as $K_2CO_3$ on $SiO_2$, $ZrO_2$ or $TiO_2$; a basic metal oxide such as MgO, CaO, BaO, ZnO, and $MnO_2$; rare-earth metal oxides such as $La_2O_3$, $CeO_2$, $Y_2O_3$, $Sm_2O_3$, and $Pr_2O_3$; mixed rare-earth metal oxides such as $La_2O_3/ZrO_2$, $ZnO/La_2O_3$, $Y_2O_3/ZrO_2$, $CeO_2/ZrO_2$, and $La_2O_3/SiO_2$; or mixtures thereof.

To convert feedstocks of biological origin over a base catalyst, a triglyceride-containing feed is exposed to the catalyst under effective conditions to convert triglycerides to fatty acids, which are coupled with other acid feed components forming coupled products. The effective conditions include a temperature from 300° C. to 450° C. A liquid hourly space velocity of from 0.1 to 10 v/v/h, particularly 0.5 to 5 v/v/h, can be applied. It is not believed that hydrogen gas is required to facilitate the coupling reaction. However, in embodiments where a single reactor is used for both the basic catalyst and the hydrogenation catalyst, hydrogen will typically be present in order to facilitate the hydrogenation reaction. As a result, a hydrogen partial pressure of 1.8 MPag to 34.6 MPag will also typically be present.

The basic catalysts according to the disclosure allow for conversion of triglycerides to ketones without requiring addition of water for an initial hydrolysis reaction, although water can be optionally added to the reactor. Instead, exposing a triglyceride-containing feedstock to the base catalysts in the presence of hydrogen allows for conversion of triglycerides to a mixture of ketones.

In a particular embodiment, a catalyst selected for catalyzing the conversion of triglycerides to ketones will remain stable in the reaction environment. The conversion of triglycerides to ketones using a base catalyst results in some production of water, so catalysts that deteriorate in water may pose some difficulties in scaling up a process for commercial use.

Hydrogenation Catalyst

After carboxylic acid coupled products are formed from triglycerides or other components of a feedstock, a second catalyst is used to hydrogenate them. Particularly, the second catalyst is also suitable for isomerizing the resulting hydrogenated molecules where needed. An additional consideration in selecting a second catalyst is that the catalyst should be stable in the presence of water, due to the water generated during conversion of the triglycerides to ketones.

The hydrogenation catalyst promotes the reaction of hydrogen with olefinic unsaturation in the ketones, heavier oxygenates, and other intermediate reaction products such as those shown in FIGS. 1 and 2. It further acts to reduce carbonyl, carboxyl, hydroxyl, and other oxygen containing groups to provide the deoxygenated hydrocarbons as reaction products. Working in concert with the basic coupling catalysts, it also provides isomerization functionality, helping to introduce sufficient branching in the final hydrocarbon products, where needed, to give basestocks with suitable pour point and low temperature properties.

Catalysts suitable for hydrogenation reaction include metals such as Mo, Re, Fe, Ru, Co, Rh, Ir, Ni, Pd, Pt, Cu, Zn, as well as binary or ternary mixtures thereof supported on silica, alumina, titania, zirconia, clays such as Kieselguhr, amorphous aluminosilicates, or zeolites. For example, the catalysts include Mo, Co, Ni, Pd, Pt, and binary or ternary mixtures thereof supported on silica, alumina, amorphous aluminosilicates, clays, or Kieselguhr. In an embodiment, the catalysts are Ni supported on Kieselguhr, CoMo on gamma-alumina, and NiMo on gamma-alumina. Metal content in the catalyst ranges from 0.1 wt % to 70 wt % of the catalyst.

In one embodiment, a hydrogenation catalyst is made of a transition metal and an acidic component as support. Non-limiting examples include Ni, Co, Pd, Pt, Ru, Rh, Co—Mo, and Ni—Mo, particularly supported on an inorganic support such as alumina, amorphous aluminosilicates, acidic clays or zeolites. The acidity of the support helps introducing branching, such as methyl branching, to long-chain hydrocarbons, thus isomerizing the long-chain hydrocarbons. With the metal hydrogenation functionality and the acidic component isomerization functionality, this type of catalyst is sometimes referred to as hydroisomerization catalyst. Non-limiting examples of the hydroisomerization catalyst include metals supported on zeolites, such as noble metals on 10-ring uni-dimensional zeolites, including Pt, Pd, or a mixture thereof for the metal and ZSM-22, ZSM-23, ZSM-35, ZSM-4, ZBM-30 or ZSM-48 for the zeolite. Other zeolites that can be used include, but are not limited to, the MCM-22 family of zeolites.

Hydrogenation catalysts having hydroisomerization functionality are sometimes referred as dewaxing catalysts in the art. The dewaxing catalyst comprises a metal hydrogenation component, an acidic component such as zeolites, and a binder.

Examples of suitable hydrogenation catalysts that have a dewaxing effect comprise zeolites as the acidic component that performs dewaxing primarily by isomerizing a hydrocarbon feedstock. These hydrogenation catalysts may be preferred for use in conjunction with a basic catalyst, which tends to produce ketone intermediates that are relatively unbranched. In an embodiment, the zeolites have a uni-dimensional (or one dimensional) pore structure. Exemplary one-dimensional zeolites include ZSM-22, ZSM-12, ZSM-23, ZSM-4, ZSM-48, and ZSM-50.

Suitable zeolites include 10-member ring pore zeolites, such as EU-1, ZSM-35 (or ferrierite), ZSM-11, ZSM-57, NU-87, SAPO-11, and ZSM-22. In particular embodiments, suitable zeolites include EU-2, EU-11, ZBM-30, ZSM-48, and ZSM-23. In some particular embodiments, zeolite is ZSM-48. Note that a zeolite having the ZSM-23 structure with a silica to alumina ratio of from 20:1 to 40:1 can sometimes be referred to as SSZ-32. Other molecular sieves that are iso-structural with the above materials include Theta-1, NU-10, EU-13, KZ-1 and NU-23.

Particularly, the hydrogenation catalysts used in processes according to the disclosure have a zeolite component with a low ratio of silica to alumina. For example, for ZSM-48, the ratio of silica to alumina in the zeolite can be less than 200:1, or less than 110:1, or less than 100:1, or less than 90:1, or less than 80:1. In various embodiments, the ratio of silica to alumina is from 30:1 to 200:1, 60:1 to 110:1, or 70:1 to 100:1.

The hydrogenation catalysts with dewaxing for use with basic catalysts also include a metal hydrogenation component. The metal hydrogenation component is typically a Group VI and/or a Group VIII metal. In various embodiments, the metal hydrogenation component is a Group VIII noble metal. In non-limiting fashion, the metal hydrogenation component is Pt, Pd or a mixture thereof. In another embodiment, the metal hydrogenation component is a combination of a non-noble Group VIII metal and a Group VI metal. Suitable combinations include Ni, Co or Fe with Mo or W, particularly Ni with Mo or W.

The metal hydrogenation component may be added to the catalyst in any convenient manner. One technique for adding the metal hydrogenation component is by incipient wetness. For example, after combining a zeolite and a hydrothermally stable binder, the combined zeolite and binder are extruded into catalyst particles. The catalyst particles are exposed to a solution containing a suitable metal precursor containing the Group VI or Group VIII metal. Alternatively, metal can be added to the catalyst by ion exchange, where a metal precursor is added to a mixture of zeolite (or zeolite and binder) prior to extrusion.

In various embodiments, the amount of metal in the catalyst is at least 0.1 wt % based on catalyst, at least 0.15 wt %, at least 0.2 wt %, at least 0.25 wt %, at least 0.3 wt %, or at least 0.5 wt % based on catalyst. In exemplary fashion, the amount of metal in the catalyst is 20 wt % or less based on catalyst, 10 wt % or less, 5 wt % or less, 2.5 wt % or less, 1 wt % or less. For embodiments where the metal is Pt, Pd, another Group VIII noble metal, or a combination thereof, the amount of metal is from 0.1 to 5 wt %, from 0.1 to 2 wt %, from 0.25 to 1.8 wt %, or from 0.4 to 1.5 wt %, in non-limiting examples. For embodiments where the metal is a combination of a non-noble Group VIII metal with a Group VI metal, the combined amount of metal is from 0.5 wt % to 20 wt %, or 1 wt % to 15 wt %, or 2.5 wt % to 10 wt %, by way of non-limiting example.

Hydrothermally Stable Binders and Hydrogenation Catalysts

In various embodiments, a second catalyst comprises a hydrogenation catalyst which is bound using a binder to increase mechanical strength and stability of the catalyst in the presence of water under effective hydrogenation conditions. Such a binder is referred to herein as a hydrothermally stable binder. Non-limiting examples of suitable binders are refractory oxides such as silica, alumina, silica-alumina, titania, zirconia, ceria, and mixtures thereof.

In particular embodiments, a hydrothermally stable binder is selected from metal oxides such as titanium oxides, zirconium oxides, cerium oxides, or a combination thereof (e.g., $TiO_2$, $ZrO_2$, $CeO_2$ and a mixture thereof). In some embodiments, the catalyst for hydrogenation and isomerization includes a binder material that provides enhanced activity and/or stability for hydrogenation and isomerization, such as a titania binder.

Optionally, the hydrogenation catalysts are formulated using a low surface area binder, where a low surface area binder is one with a surface area of 100 $m^2/g$ or less, 80 $m^2/g$ or less, or 70 $m^2/g$ or less. In various embodiments, the binder and the zeolite particle size are selected to provide a catalyst with a desired ratio of micropore surface area to total surface area. In hydrogenation catalysts used according to the disclosure, and in exemplary fashion those used along with a basic material as coupling catalyst, the micropore surface area corresponds to surface area from the uni-dimensional pores of zeolites in the hydrogenation catalyst. The total surface area corresponds to the micropore surface area plus the external surface area. Any binder used in the catalyst will not contribute to the micropore surface area and will not significantly increase the total surface area of the catalyst. The external surface area represents the balance of the surface area of the total catalyst minus the micropore surface area. Both the binder and zeolite can contribute to the value of the external surface area. In particular embodiments, the ratio of micropore surface area to total surface area for a hydrogenation catalyst will be equal to or greater than 25%.

A zeolite can be combined with a binder in any convenient manner. For example, a bound catalyst can be produced by starting with powders of both the zeolite and binder, combining and mulling the powders with added water to form a mixture, and then extruding the mixture to produce a bound catalyst of a desired size. Extrusion aids can also be used to modify the extrusion flow properties of the zeolite and binder mixture.

In yet another embodiment, a binder composed of a mixture of two or more metal oxides is used. In the case where the two or more metal oxides of the binder have different surface areas, the weight percentage of the binder with lower surface area may be greater than the weight percentage of the binder having higher surface area. Alternatively, if both metal oxides used for forming a mixed metal oxide binder have a sufficiently low surface area, the proportions of each metal oxide in the binder are less important. When two or more metal oxides are used to form a binder, the two metal oxides can be incorporated into the catalyst by any convenient method. In one example, a first binder is mixed with the zeolite during formation of the zeolite powder, such as during spray drying. The spray dried zeolite/binder powder is then mixed with the second metal oxide binder prior to extrusion.

Reaction Conditions and Process Configurations

The methods of this disclosure can be carried out stepwise using multi-reactors or in a single reactor. In a particular embodiment, reaction of the feedstock with the catalysts or catalyst components is conveniently carried out in a single reactor, without the necessity of isolating and purifying the product of reaction steps, as necessitated by the multi-reactor processes of the prior art. It has been found that reaction proceeds from feedstock to lube base stock hydrocarbon under a single set of pressure, temperature, and time conditions in the presence of hydrogen. The process simplifies production of basestocks from renewable feeds in that only a single reactor is dealt with.

In particular embodiments for carrying out the reaction, a layered bed or a stacked catalyst bed is used. In this configuration, a first catalyst that is mainly responsible for coupling the carboxylic acids to produce molecules of suitable carbon number is disposed in the reactor so as to come into contact with the feedstock before the reacted feedstock contacts the second catalyst (the hydrogenation catalyst). Flow of the reacting material over the catalysts is controlled by varying the pressure, feed rate, and other parameters. Residence time for contact with the catalyst compositions is naturally controlled in the same way. In various embodiments, the method is adapted for batch-wise or for continuous production of lube base stock.

Hydrogen can be present throughout the reactor, and is consumed by the reactants during the hydrogenation step. Advantageously, it was found that the presence of hydrogen did not adversely affect the carboxylic acid coupling reactions believed to be catalyzed primarily by the basic catalysts. During the fatty acid coupling, hydrogen transfer reactions can lead to formation of coke molecules, which can cause catalyst deactivation. In various embodiments, the presence of hydrogen can inhibit hydrogen transfer and improve catalyst life.

Temperature and pressure of the reactor and reactants is selected depending on the throughput and turnover required. Non-limiting examples of temperatures include 100 to 500° C., 200 to 400° C., and 250 to 400° C. Hydrogen partial pressure is used in the range of from 1.8 to 34.6 MPag (250 to 5000 psig) or 4.8 to 20.8 MPag, by way of non-limiting example. Also in non-limiting fashion, a liquid hourly space velocity is from 0.2 to 10 v/v/hr, or 0.5 to 3.0, and a hydrogen circulation rate is 35.6 to 1781 $m^3/m^3$ (200 to 10,000 scf/B), particularly 178 to 890.6 $m^3/m^3$ (1000 to 5000 scf/B). Further non-limiting examples of conditions are given in working examples. In particular embodiments, the method is carried out in a batch or flow reactor at a temperature of 275 to 400° C., a pressure of 300 to 700 psig, and a liquid hourly space velocity of 0.1 to 10 v/v/h under static or flowing gas comprising $N_2$ or $H_2$.

Loading of the catalyst is 1 to 30% by weight of the weight of the feedstock in the reactor, for example 2 to 20%, or 5 to 10% by weight. The reaction time or residence time can range from 5 minutes to 50 hours depending on types of catalysts used, reaction temperature and the amount (wt %) of catalyst in the reactor. In a particular embodiment, a residence time is 10 minutes to 10 hours. Shorter residence time gives better efficiency for reactor usage. Longer residence time ensures high conversion to pure hydrocarbons. Usually an optimized reactor time is most desirable.

In various embodiments, the duration of the reaction (or the average residence time in the reactor for a continuous process) is 1-48 hours, 1-20 hours, 12-36 hours, or 24-30 hours. In various embodiments, the reactions are carried out in a fixed bed reactor, a continuous stir tank reactor, or a batch reactor. In any of these operations, it is advantageous to maintain partial pressure of hydrogen above 300 psi, above 400 psi, above 500 psi, above 600 psi, or above 700 psi. During conversion, carbon dioxide and water generated from the action of the acidic or basic catalyst on the feedstock are present in gaseous form, and thus increase the total reactor pressure. Under this condition, it can be important to maintain hydrogen partial pressure. By way of non-limiting example, this can be achieved by intermittently purging the reactor gas and re-charging with hydrogen gas in batch or CSTR operation. Alternatively, in a fixed bed operation, this can be achieved by withdrawing reactor gas at different locations along the fixed bed reactor; or alternatively by stage injection of hydrogen. Other means to maintain hydrogen pressure are also possible.

In an embodiment, a method of this disclosure is carried out with a basic catalyst selected from $La_2O_3/ZrO_2$, $La_2O_3/ZnO$ and $Y_2O_3/ZrO_2$, where the La content is 5 to 10 wt % in the mixture, and a hydrogenation catalyst which is Pt supported on ZSM-48 with a binder selected from $TiO_2$, $ZrO_2$ and a mixture thereof (0.3 to 1% Pt on the catalyst) or ZSM-48/$NiWO_x$ (20 to 40% $NiWO_x$) at a temperature of 300 to 400° C. under $H_2$ partial pressure of 500 to 800 psig.

There are several alternatives for how to incorporate the hydrogenation catalyst in the reaction system. One option is to configure the carboxylic acid coupling catalyst and the hydrogenation catalyst as stacked beds. In this type of configuration, a reactor or reaction system will contain one or more initial beds of carboxylic acid coupling catalyst for converting the feed to one or more of ketones, heavier oxygenates. As described above, exposing a carboxylic acid such as fatty acid or triglyceride-containing feed to the one or more initial beds of carboxylic acid coupling catalysts (first catalyst) will result in production of an effluent containing ketones or heavier oxygenates. The effluent containing these oxygenates is then exposed to one or more beds of a hydrogenation catalyst under effective hydrogenation conditions. This can result in hydrogenation of products formed by the action of the first catalyst.

Where needed, the hydrogenation catalyst can introduce branches into the final hydrocarbon products to provide a dewaxing function. For feeds containing triglycerides with only saturated fatty acid side chains, the combination of coupling fatty acids with other carboxylic acids and hydrogenation may give relatively unbranched hydrocarbons. For feeds containing triglycerides with both saturated and unsaturated fatty acid side chains, the combination of coupling fatty acids with other carboxylic acids and hydrogenation will give mixtures of branched hydrocarbons (containing one or more branches of various lengths in the range of 1 to 10 carbons) and naphthenics substituted with various lengths of hydrocarbon chains. Of course, if the side chains of the triglycerides contain other types of heteroatoms, such as nitrogen or sulfur, other types of molecules may be generated.

An alternative configuration is to combine both the carboxylic acid coupling catalyst and the hydrogenation catalyst in the same catalyst bed. In this type of configuration, both the coupling catalyst and the hydrogenation catalyst are exposed to the initial feed. In this type of configuration, some amount of the initial triglycerides in the feed will be converted to diesel boiling range molecules. This is believed to be due to the ability of the hydrogenation catalyst to deoxygenate the side chains of the triglycerides (or of an intermediate product of the triglycerides, such as fatty acids) before reaction to form carboxylic acid coupled products can occur.

Figure 4:
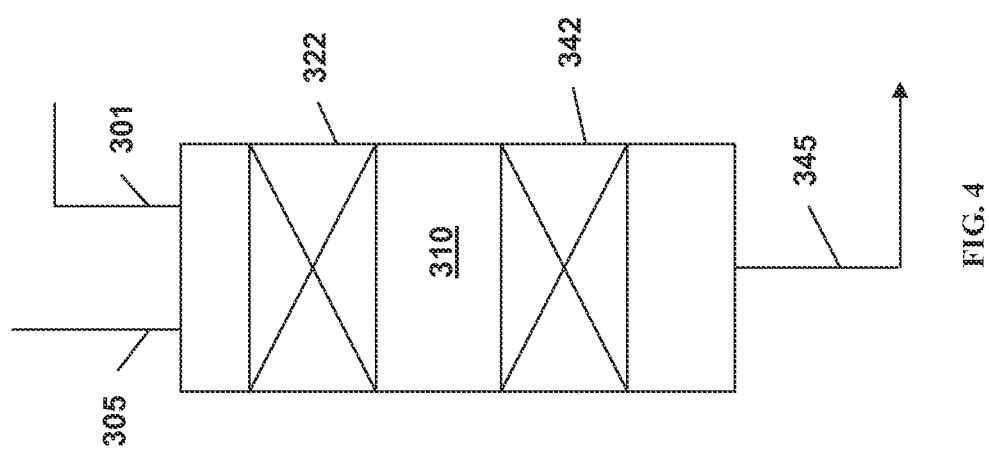
FIG. 4 shows a scheme of a reaction system suitable for performing a process according to an aspect of the disclosure.

FIG. 4 schematically illustrates an example of a reactor suitable for the processes described herein. In FIG. 4, reactor 310 is shown as containing reaction zones 322 and 342. Each reaction zone can correspond to one or more catalyst beds. Alternatively, one or more reactors may be used in a cascade configuration, and any convenient number of reaction zones may be used within a reactor.

In stacked bed configuration, reaction zone 322 can contain one or more catalyst beds of a basic catalyst. The feedstock 305 is introduced into reactor 310 so that the feedstock is exposed to the catalyst in the catalyst beds in reaction zone 322 prior to being exposed to the catalyst in reaction zone 342. In FIG. 4, hydrogen treat gas 301 is shown as entering reactor 310 in a co-current manner relative to the flow of the feedstock 305. Alternatively, hydrogen treat gas can be introduced into reactor 310 in other convenient manners, such as introducing the hydrogen treat gas to flow counter-current relative to feedstock 305.

After passing through reaction zone 322, the effluent is exposed to the catalyst in the one or more catalyst beds in reaction zone 342. Depending on the configuration, reaction zone 342 is an optional reaction zone. For example, in a configuration where only mixed beds of catalyst are used, only a single reaction zone 322 may be needed. The effluent from reaction zone 342 (or optionally reaction zone 322) then exits the reactor as a product effluent flow 345.

In one type of stacked bed configuration, the one or more catalyst beds in reaction zone 322 corresponds to a basic catalyst, while the one or more catalyst beds in reaction zone 342 correspond to a hydrogenation catalyst. In another type of stacked bed configuration, one or both of reaction zones 322 and 342 can contain mixed beds of a basic catalyst as well as a hydrogenation catalyst. In this type of configuration, the volume percentage of the hydrogenation catalyst is greater in the catalyst beds in reaction zone 342 as compared to the volume percentage of hydrogenation catalyst in the catalyst beds in reaction zone 322.

Still another option is to have a uniform mixture of hydrogenation catalyst and a basic catalyst within the reaction zones in the reactor. In this type of configuration, reaction zone 342 is optional, as the same or similar conditions are present throughout the reactor. Thus, all catalyst beds within the reactor can alternatively be thought of as being in reaction zone 322.

Further Processing

The product of the reaction described herein is a mixture of hydrocarbons having a carbon number in the lube base stock range. If desired, the reaction product can be hydrofinished by subjecting it to low pressure hydrogen. This process can clean up residual olefinic unsaturations and oxygenates that may result when the products are being heated in the presence of the hydrogenation catalyst, which can have some cracking power given that it may contain an acidic carrier such as a zeolite. The hydrofinishing can be carried out either in a fixed-bed or in an autoclave reactor. The catalyst can be either noble metal (Pd, Pt, Rh, to Ru, Ir, or combination thereof) or non-noble metal (Co, Ni, Fe), particularly supported on a support such as clay, alumina, aluminosilicate, silica, titania and zirconia. The weight hourly space velocity can be in the range of 0.5 to 10 $h^{-1}$, under a hydrogen pressure in the range of ambient to 30 MPag, and a temperature from 150° C. to 400° C.

The product of the catalytic reactions described herein comprises hydrocarbons in the lube base stock range (above $C_{20}$, for example $C_{28}$ or higher such as $C_{28}$-$C_{300}$), with possible co-products in the diesel fuel (<$C_{20}$) range.

The basestock has pour point lower than 0° C., particularly lower than −10° C., more particularly lower than −20° C. The basestock has a kinematic viscosity Kv100 of 3 to 100 cSt, and a viscosity index of at least 90.

The basestock is significantly free of carbonyl groups as measured by Infrared (IR) spectroscopy, that is, there is no peak in the 1600-1800 $cm^{-1}$ region. The product is also significantly free of vinylic hydrogen as measured by Nuclear Magnetic Resonance (NMR) spectroscopy. In the $^1$H NMR spectrum, the vinylic hydrogen is less than 1%, particularly less than 0.5%, more particularly less than 0.3% of total hydrogen.

As a lube stock, the product can be formulated with conventional lube additives such as antiwear agents, antioxidants, VI improvers, biocides, preservatives, extreme pressure additives, and the like to formulate lubricant compositions.

EXAMPLES

Example 1

Coupling of 1,4-Naphthalene Dicarboxylic Acid and Stearic Acid Over Hydrotalcite A process comprising coupling of 1,4-naphthalene dicarboxylic acid and stearic acid over hydrotalcite (Pural MG 50, $Mg_{2x}Al_2(OH)_{4x+4}CO_3.nH_2O$, $MgO:Al_2O_3=50:50$) was performed at 325° C., 400 psi $H_2$ and a catalyst loading of 0.34 g. The weight ratio of stearic acid to 1,4-naphthalene dicarboxylic acid was 3. After 24 hours at reaction conditions, the starting compounds were completely converted and a mass balance of 91.2% was obtained.

FIG. 1 shows products that can be formed by coupling of compounds containing carboxylic acid functionalities. Both homo-coupling of stearic acid and cross-coupling between stearic acid and naphthalene dicarboxylic acid can occur.

Figure 5:
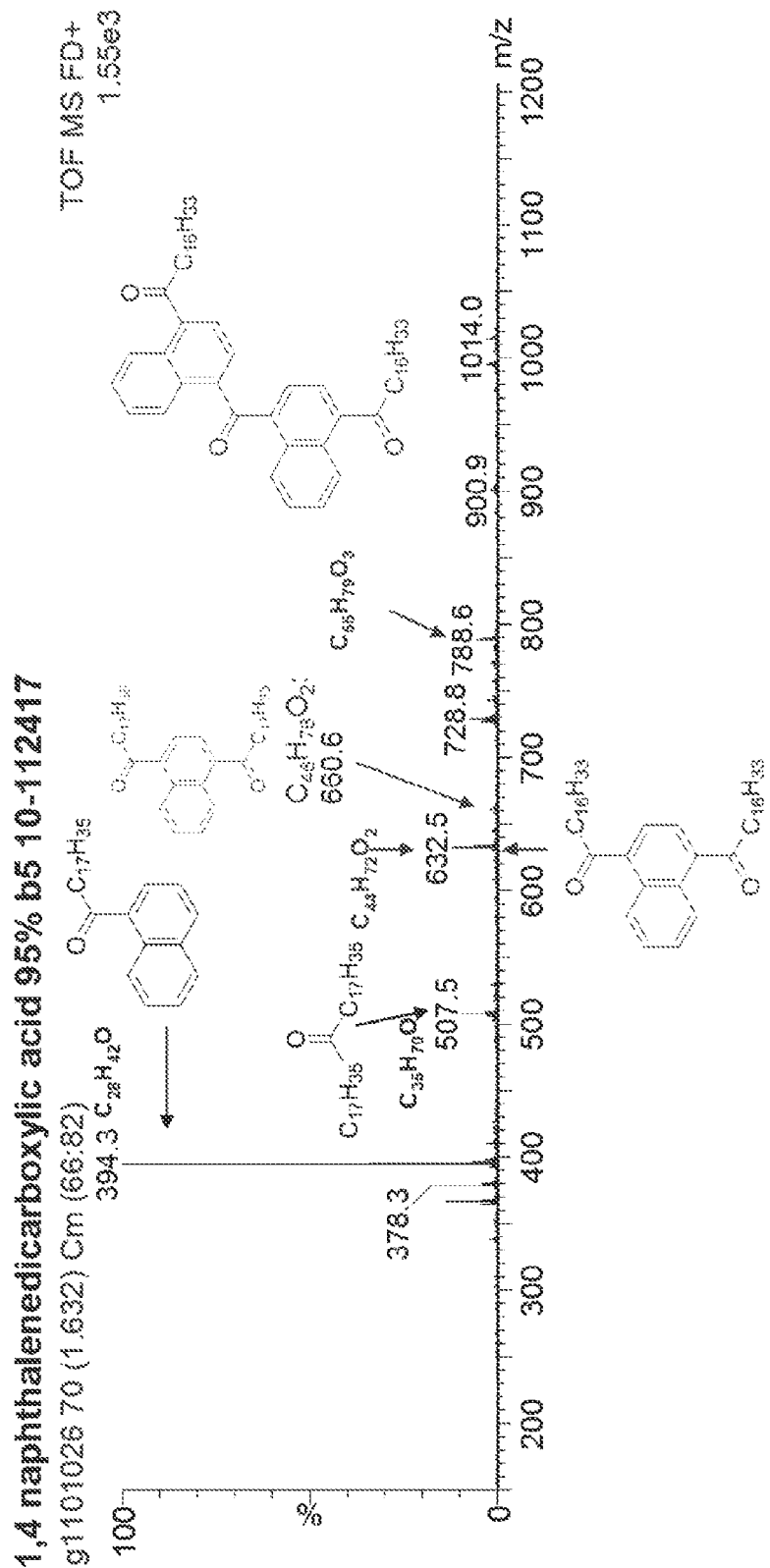
FIG. 5 is a GFD-TOF mass spectrum of reaction products from a process using 1,4-naphthalenedicarboxylic acid and stearic acid (Example 1).

FIG. 5 (a GFD-TOF mass spectrum of the products obtained from this reaction) shows that both homo- and cross-coupling occurred. The homo-coupling of stearic acid gave a symmetrical ketone ($C_{35}H_{70}O$, mass=507.5). The cross-coupling between stearic and naphthalene dicarboxylic acids gave a number of products, as shown in FIG. 5 (mass of 394.3, 632.5, 660.6). It also showed that naphthalene dicarboxylic acid can also react with itself to form a symmetrical aromatic ketone which further reacts with stearic acid forming even larger ketones (mass=788.6).

The acid coupling reaction generates one mol of water and one mol of $CO_2$ for every two units of acid coupled. Based on this stoichiometry, a mass balance of 91.7% can be calculated, assuming that both acids are 100% converted and 1 mol of $CO_2$ is lost for every two units of acid being coupled. The calculated mass balance matches very well with the actual mass balance of 91.2%, affirming a near complete conversion of the starting materials, as shown by the GC/MS trace.

Figure 6:
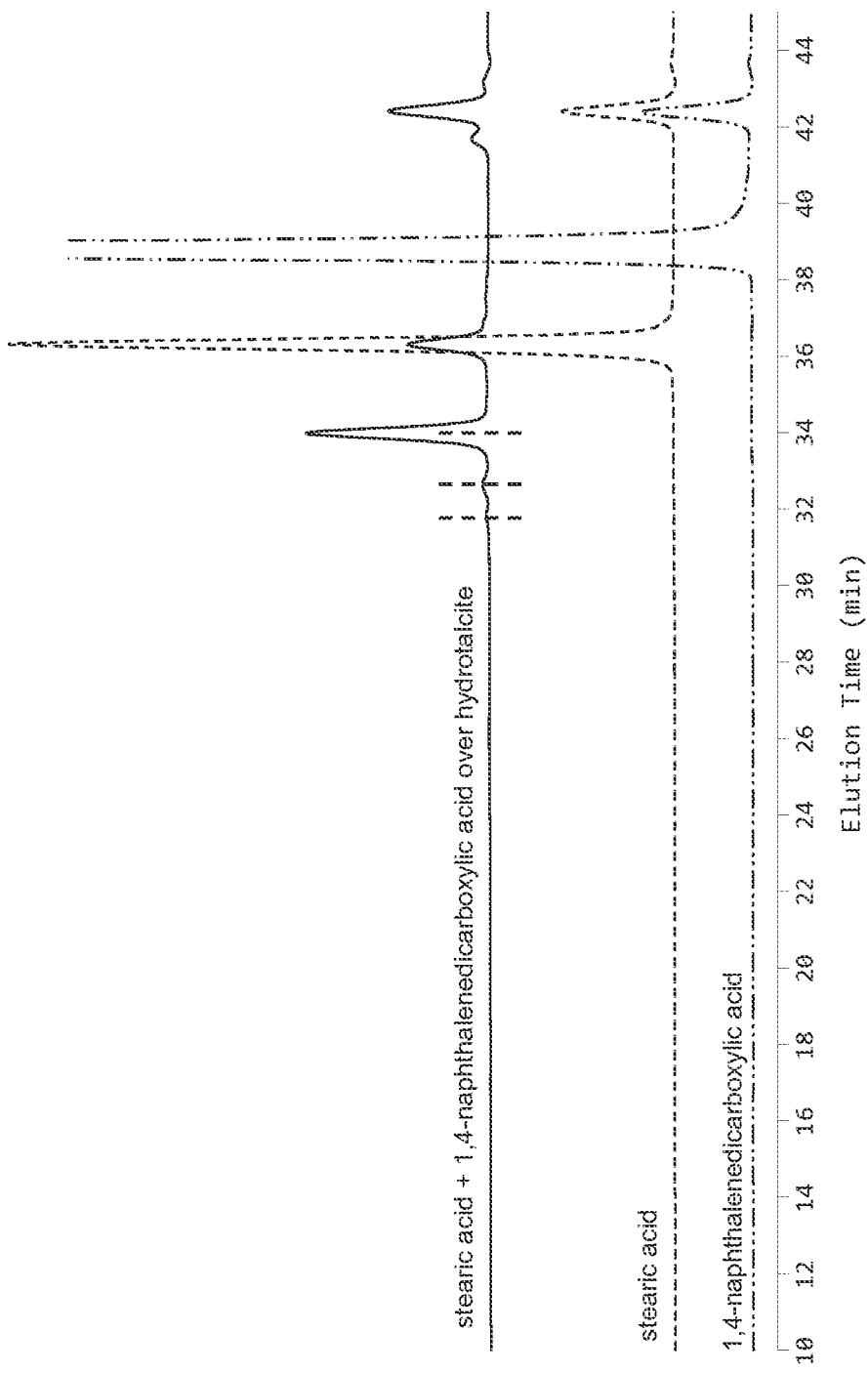
FIG. 6 is a gel permeation chromatography (GPC) of reaction products from a process using 1,4-naphthalenedicarboxylic acid and stearic acid (Example 1).

The coupling products were also analyzed by Gel Permeation Chromatography (GPC) and the results are shown in FIG. 6. Consistent with the mass spectroscopy results, high molecular weight coupling products were observed (peaks marked with dashed vertical lines). The ketones formed from the coupling can be hydrogenated to give high molecular weight alkylated naphthalenes.

Example 2

Coupling of Stearic Acid and Citric Acid Over Hydrotalcite

The High Pressure/Heated Orbital Shaker System (HiP/HOSS) was used for a method comprising ketonic decarboxylic coupling of various carboxylic acid species such as free fatty acids, citric acid, and naphthalene dicarboxylic acid as well as of the triglycerides tristearin and soy oil (see FIG. 7). The products from these batch experiments were analyzed by GC/MS. Selected samples were analyzed by FID, ESI and GFD-TOF mass spectroscopy.

The catalyst employed in these experiments was a hydrotalcite material (Pural MG 50, $Mg_{2x}Al_2(OH)_{4x+4}CO_3.nH_2O$, $MgO:Al_2O_3=50:50$) that was provided by Sasol. Most coupling experiments were performed at 325° C. and 400 psi $H_2$ for 24 hours at a WHSV of 0.2 to 2 $hr^{-1}$. Hydrogen is not required for the coupling but was added to the experiments due to simultaneously run experiments that required a reducing atmosphere.

Figure 8:
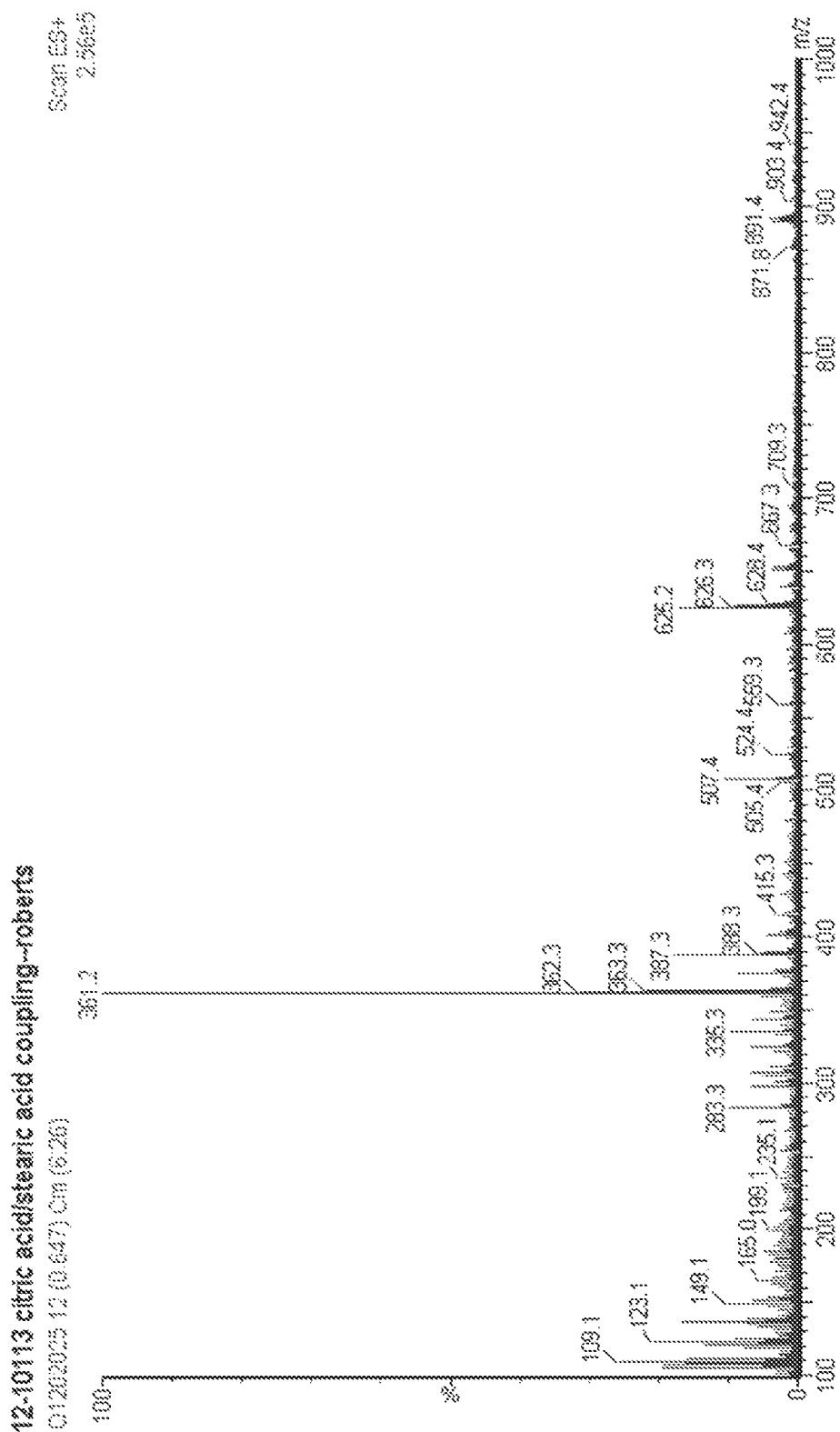
FIG. 8 is a GFD-TOF mass spectrum of reaction products from a process using citric acid and stearic acid (Example 2).

In the coupling reaction, 3 g of stearic acid and 0.68 g of citric acid were reacted over 0.5 g hydrotalcite for 4 hours at 350° C. and 400 psi hydrogen. An ESI spectrum of the generated sample was measured. Although the three peaks at m/z=361, 625 and 891 do not correspond to the exact molecular weights of the expected products, this pattern shows the formation of products representing single, di- and tri-coupling of the stearic acid acyl chain to the citric acid backbone as shown in FIG. 8.

All documents described herein are incorporated by reference herein, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. Likewise, the term "comprising" is considered synonymous with the term "including" for purposes of Australian law.

When numerical lower limits and numerical upper limits are listed herein, ranges from any lower limit to any upper limit are contemplated.

While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

What is claimed is:

1. A method for producing a lube basestock, the method comprising:
    contacting a compound of Formula (I) and a feedstock of biological origin to form a ketone in the presence of a first catalyst comprising a basic material:

Formula (I)

wherein $R^1$ is selected from the group consisting of cyclic hydrocarbyl and aryl, wherein $R^1$ has one or more optional substitutions selected from the group consisting of $-R^a$, $-OR^a$, $-C(O)R^a$, and $-C(O)OR^a$, wherein $R^a$ is H or $C_1$-$C_6$ alkyl group, and n is 3, 4 or 5; and
    hydrogenating the ketone to a hydrocarbon in the presence of water and a second catalyst comprising a hydrogenation catalyst and a hydrothermally stable binder, wherein the hydrocarbon is a lube basestock.

2. The method according to claim 1, wherein the hydrothermally stable binder comprises $TiO_2$, $ZrO_2$ or $CeO_2$.

3. The method according to claim 1, further comprising hydroisomerizing the hydrocarbon formed by hydrogenating the ketone.

4. The method according to claim 1, wherein n is 3.

5. The method according to claim 1, wherein the feedstock of biological origin comprises one or more components selected from the group consisting of fatty acid, fatty acid ester, fatty alcohol, fatty olefin, mono-glyceride, di-glyceride, tri-glyceride, phospholipid and saccharolipid.

6. The method according to claim 5, wherein the feedstock of biological origin is selected from the group consisting of rapeseed oil, soy bean oil, palm oil, camelina oil, jatropha oil, jojoba oil, fish oil, lard, beef tallow, and algae oil.

7. The method according to claim 1, comprising providing the feedstock of biological origin as a solution in a hydrocarbon solvent.

8. The method according to claim 1, wherein $R^1$ is phenyl or naphthalenyl and n is 3.

9. The method according to claim 1, wherein the feedstock of biological origin comprises stearic acid or tristearin.

10. The method according to claim 1, wherein the first catalyst is selected from the group consisting of basic clay, alkali impregnated support, basic metal oxide, and a mixture thereof.

11. The method according to claim 10, wherein the first catalyst comprises a basic metal oxide selected from the group consisting of hydrotalcite, MgO, CaO, BaO, ZnO, $MnO_2$, $K_2CO_3$ supported on $SiO_2$, $K_2CO_3$ supported on $ZrO_2$, and $K_2CO_3$ supported on $TiO_2$.

12. The method according to claim 10, wherein the first catalyst comprises a basic metal oxide selected from the group consisting of $La_2O_3$, $CeO_2$, $Y_2O_3$, $Sm_2O_3$, $Pr_2O_3$, $La_2O_3/ZrO_2$, $ZnO/La_2O_3$, $Y_2O_3/ZrO_2$, $CeO_2/ZrO_2$, and $La_2O_3/SiO_2$.

13. The method according to claim 1, wherein the hydrogenation catalyst comprises a metal hydrogenation component selected from the group consisting of Ni, Co, Pd, Pt, Ru, Rh, Co—Mo, Ni—Mo, Ni—W, and Co—W, and wherein the metal hydrogenation component is supported on an inorganic support selected from the group consisting of silica, alumina, titania, zirconia, zeolite, carbon, and gamma-alumina.

14. The method according to claim 13, wherein the hydrogenation catalyst is Pt supported on a support selected from the group consisting of zeolite of the faujasite, beta, or MWW family, 10-ring zeolite, and 8-ring zeolite.

15. The method according to claim 13, wherein the hydrogenation catalyst is selected from the group consisting of Ni or Pd supported on silica or carbon; Co—Mo or Co—W supported on gamma-alumina; and Ni—Mo or Ni—W on gamma-alumina.

16. The method according to claim 1, wherein the method is carried out at a temperature of from 275 to 400° C., a pressure of from 300 to 700 psig, and a liquid hourly space velocity of from 0.1 to 10 v/v/h under static or flowing gas comprising $N_2$ or $H_2$.

17. The method according to claim 1, wherein the basic material comprises $La_2O_3/ZrO_2$, $La_2O_3/ZnO$, $Y_2O_3/ZrO_2$, or a combination thereof
wherein the hydrogenation catalyst is Pt supported on ZSM-48 or Pt supported on ZSM-48/$NiWO_x$,
wherein the hydrothermally stable binder comprises $TiO_2$, $ZrO_2$ or a mixture thereof, and
wherein the method is carried out at a temperature of from 300 to 400° C. under $H_2$ partial pressure of from 500 to 800 psig.

18. A method for producing a lube basestock, the method comprising:
coupling a compound of Formula (I) and a compound of Formula (II) in the presence of a first catalyst component comprising a basic material to produce a ketone of Formula (III):

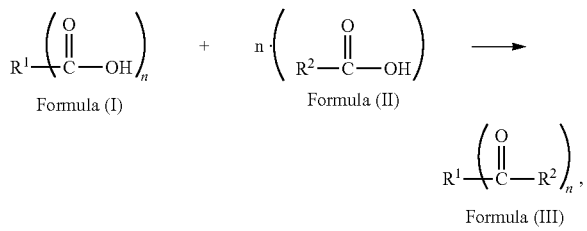

wherein each of $R^1$ and $R^2$ is independently selected from the group consisting of acyclic hydrocarbyl, cyclic hydrocarbyl, and aryl, wherein each of $R^1$ and $R^2$ independently has one or more optional substitutions selected from the group consisting of —$R^a$, —$OR^a$, —$C(O)R^a$, and —$C(O)OR^a$, wherein $R^a$ is H or $C_1$-$C_6$ alkyl group, and n is 3, 4 or 5; and
hydrogenating the ketone of Formula (II) to a hydrocarbon with a second catalyst comprising a hydrogenation catalyst and a hydrothermally stable binder wherein the hydrocarbon is a lube basestock.

19. The method according to claim 18, wherein the hydrothermally stable binder comprises $TiO_2$, $ZrO_2$ or $CeO_2$.

20. The method according to claim 18, wherein $R^1$ is phenyl or naphthalenyl and n is 3.

21. The method according to claim 18, wherein the compound of Formula (I) is selected from the group consisting of 1,2,3-propanetricarboxylic acid and citric acid; the compound of Formula (II) is a saturated or unsaturated $C_{10}$-$C_{22}$ fatty acid; and the first catalyst comprises MgO or hydrotalcite.

22. The method according to claim 21, wherein the compound of Formula (II) is selected from the group consisting of capric acid, lauric acid, myristic acid, palmitic acid, stearic acid, oleic acid, linoleic acid, arachidic acid, and behenic acid.

23. The method according to claim 18, wherein the first catalyst comprises a basic material selected from the group consisting of hydrotalcites; a basic metal oxide comprising MgO, CaO, BaO, ZnO, $MnO_2$, $K_2CO_3$ supported on $SiO_2$ $K_2CO_3$ supported on $ZrO_2$, or a combination thereof; $K_2CO_3$ supported on $TiO_2$; and a mixed rare earth metal oxide comprising $La_2O_3$, $CeO_2$, $Y_2O_3$, $Sm_2O_3$, $Pr_2O_3$, $La_2O_3/ZrO_2$, $ZnO/La_2O_3$, $Y_2O_3/ZrO_2$, $CeO_2/ZrO_2$, $La_2O_3/SiO_2$, or a combination thereof.

24. The method according to claim 18, wherein the second catalyst comprises a metal hydrogenation component selected from the group consisting of Ni, Co, Pd, Pt, Ru, Rh, Co—Mo, Ni—Mo, Ni—W, and Co—W, and wherein the metal hydrogenation component is supported on zeolite selected from the group consisting of ZSM-22, ZSM-12, ZSM-23, ZSM-4, ZSM-48 and ZSM-50.

25. The method according to claim 18, wherein the method is carried out at a temperature of from 275 to 400° C., a pressure of from 300 to 700 psig, and a liquid hourly space velocity of from 0.1 to 10 v/v/h under static or flowing gas comprising $N_2$ or $H_2$.

26. A method for producing a lube basestock, the method comprising:
contacting a compound of Formula (I) and the feedstock of biological origin in the presence of a first catalyst comprising a basic material and a second catalyst comprising a hydrogenation catalyst and a hydrothermally stable binder in a single reactor, the compound of Formula (I) and a feedstock of biological origin being contacted with the second catalyst in the presence of water:

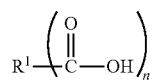

Formula (I)

wherein $R^1$ is selected from the group consisting of acyclic hydrocarbyl, cyclic hydrocarbyl, and aryl, wherein $R^1$ has one or more optional substitutions selected from the group consisting of —$R^a$, —$OR^a$, —$C(O)R^a$, and —$C(O)OR^a$, wherein $R^a$ is H or $C_1$-$C_6$ alkyl group, and n is 3, 4 or 5, wherein said contacting produces a lube basestock.

27. The method according to claim 26, wherein the hydrothermally stable binder comprises $TiO_2$, $ZrO_2$ or $CeO_2$.

28. The method according to claim 26, comprising contacting the feedstock of biological origin sequentially with the first catalyst in a first zone of the reactor and with the hydrogenation catalyst in a second zone of the reactor.

29. The method according to claim 26, wherein $R^1$ is phenyl or naphthalenyl and n is 3.

30. The method according to claim 26, wherein the compound of Formula (I) is selected from the group consisting of 1,2,3-propanetricarboxylic acid and citric acid; the feedstock of biological origin is selected from the group consisting of rapeseed oil, soy bean oil, palm oil, camelina oil, jatropha oil, jojoba oil, fish oil, lard, beef tallow, and algae oil; and the first catalyst comprises MgO or hydrotalcite.

31. The method according to claim 26, wherein the feedstock of biological origin comprises stearic acid or tristearin.

32. The method according to claim 26, wherein the first catalyst comprises a basic catalyst selected from the group consisting of hydrotalcites; a basic metal oxide comprising MgO, CaO, BaO, ZnO, $MnO_2$, $K_2CO_3$ supported on $SiO_2$, $K_2CO_3$ supported on $ZrO_2$, or a combination thereof; $K_2CO_3$ supported on $TiO_2$; and a mixed rare earth metal oxide comprising $La_2O_3$, $CeO_2$, $Y_2O_3$, $Sm_2O_3$, $Pr_2O_3$, $La_2O_3/ZrO_2$, $ZnO/La_2O_3$, $Y_2O_3/ZrO_2$, $CeO_2/ZrO_2$, $La_2O_3/SiO_2$, or a combination thereof.

33. The method according to claim 26, wherein the second catalyst comprises a metal hydrogenation component selected from the group consisting of Ni, Co, Pd, Pt, Ru, Rh, Co—Mo, Ni—Mo, Ni—W, and Co—W, and wherein the metal hydrogenation component is supported on zeolite selected from the group consisting of ZSM-22, ZSM-12, ZSM-23, ZSM-4, ZSM-48 and ZSM-50.

34. The method according to claim 26, wherein the method is carried out at a temperature of from 275 to 400° C., a pressure of from 300 to 700 psig, and a liquid hourly space velocity of from 0.1 to 10 v/v/h under static or flowing gas comprising $N_2$ or $H_2$.

\* \* \* \* \*